US010815337B2

(12) United States Patent
Gillet et al.

(10) Patent No.: US 10,815,337 B2
(45) Date of Patent: Oct. 27, 2020

(54) ETHER AMINE COMPOUNDS AND USE THEREOF AS FLOTATION COLLECTOR

(71) Applicant: ARKEMA FRANCE, Colombes (FR)

(72) Inventors: Jean-Philippe Gillet, Brignais (FR); Eric Jorda, Lyons (FR)

(73) Assignee: Arkema France, Colombes (FR)

( * ) Notice: Subject to any disclaimer, the term of this patent is extended or adjusted under 35 U.S.C. 154(b) by 134 days.

(21) Appl. No.: 15/756,116

(22) PCT Filed: Sep. 9, 2016

(86) PCT No.: PCT/FR2016/052277
§ 371 (c)(1),
(2) Date: Feb. 28, 2018

(87) PCT Pub. No.: WO2017/042514
PCT Pub. Date: Mar. 16, 2017

(65) Prior Publication Data
US 2018/0251603 A1    Sep. 6, 2018

(30) Foreign Application Priority Data
Sep. 10, 2015  (FR) ..................... 15 58435

(51) Int. Cl.
| | |
|---|---|
| C07C 213/02 | (2006.01) |
| C08G 73/02 | (2006.01) |
| C10M 133/04 | (2006.01) |
| B03D 1/004 | (2006.01) |
| C07C 217/08 | (2006.01) |
| C08G 65/333 | (2006.01) |
| C08G 65/26 | (2006.01) |
| C07C 255/25 | (2006.01) |
| B03D 1/01 | (2006.01) |
| C07C 255/13 | (2006.01) |
| C08L 63/00 | (2006.01) |

(52) U.S. Cl.
CPC ......... *C08G 73/024* (2013.01); *B03D 1/0043* (2013.01); *B03D 1/01* (2013.01); *C07C 213/02* (2013.01); *C07C 217/08* (2013.01); *C07C 255/13* (2013.01); *C07C 255/25* (2013.01); *C08G 65/2606* (2013.01); *C08G 65/2618* (2013.01); *C08G 65/33365* (2013.01); *C08G 65/33368* (2013.01); *C10M 133/04* (2013.01); *B03D 2201/02* (2013.01); *B03D 2203/04* (2013.01); *C08L 63/00* (2013.01); *C08L 2205/22* (2013.01); *C08L 2312/00* (2013.01); *C10M 2215/042* (2013.01)

(58) Field of Classification Search
None
See application file for complete search history.

(56) References Cited

U.S. PATENT DOCUMENTS

| | | | | |
|---|---|---|---|---|
| 4,324,739 A | * | 4/1982 | Zondler | ............ C08G 59/4014 |
| | | | | 558/445 |
| 5,196,589 A | | 3/1993 | O'Lenick, Jr. et al. | |
| 6,260,561 B1 | | 7/2001 | Gartner et al. | |
| 2006/0052598 A1 | * | 3/2006 | Burton | ............... B01D 15/1878 |
| | | | | 544/180 |

FOREIGN PATENT DOCUMENTS

| | | |
|---|---|---|
| EP | 0 533 552 A1 | 3/1993 |
| EP | 1 219 597 A1 | 7/2002 |
| WO | WO 2005/014491 A1 | 2/2005 |

OTHER PUBLICATIONS

Alkoxypropylamines prepn—by hydrogenation of crude alkaxyprapianitrile on Raney nickel at 110-140 deg. C, Derwent, XP002192710 (1974).
International Search Report for International Application No. PCT/FR2016/052277, dated May 12, 2016.
Perdriau et al., Angewandte Chemie Int'l Edition, 54(14):4236-40 (2015).
Watanabe et al. Journal of the American Oil Chemists Society, 68(1):44-46 (1991).

* cited by examiner

*Primary Examiner* — Sudhakar Katakam
*Assistant Examiner* — Jennifer C Sawyer
(74) *Attorney, Agent, or Firm* — RatnerPrestia

(57) ABSTRACT

The present invention relates to a compound of formula (I):

$$\text{R}_1\text{-}\underset{\text{R}_3}{\underset{|}{\text{CH}}}\text{-R}_2\text{-O-}\left[\underset{\text{R}_3}{\underset{|}{\text{CH}}}\text{-}\underset{\text{R}_4}{\underset{|}{\text{CH}}}\text{-O}\right]_n\left[\underset{\text{R}_6}{\underset{|}{\text{CH}}}\text{-}\underset{\text{R}_7}{\underset{|}{\text{CH}}}\text{-}\underset{\text{R}_5}{\underset{|}{\text{CH}}}\text{-NH}\right]_m\text{H} \quad \text{(I)}$$

in which: the $R_1$ and $R_2$ groups, which may be identical or different, are, independently of one another, a saturated or unsaturated, linear, branched or cyclic hydrocarbon group having from 1 to 15 carbon atoms, preferably from 1 to 10 carbon atoms; the $R_3$ and $R_4$ groups, which may be identical or different, are selected, independently of one another, from a hydrogen atom, a methyl group or an ethyl group; the R, $R_6$ and $R_7$ groups, which may be identical or different, are selected, independently of one another, from a hydrogen atom or an alkyl group comprising from 1 to 6 carbon atoms; n is an integer of 0 to 20; and m is an integer of 1 to 6.

13 Claims, No Drawings

ETHER AMINE COMPOUNDS AND USE THEREOF AS FLOTATION COLLECTOR

CROSS-REFERENCE TO RELATED APPLICATIONS

This is the U.S. National Phase of International Application No. PCT/FR2016/052277, filed Sep. 9, 2016, which claims priority to French Application No. 1558435, filed Sep. 10, 2015. The disclosure of each of these applications is incorporated herein by reference in its entirety for all purposes.

FIELD OF THE INVENTION

The present invention relates to the general field of ether amines. The ether amine family represents a unique family of chemical products offering a wide range of properties. Specifically, they may be used in particular as lubricants, cationic surfactants, ore flotation collectors, or as corrosion inhibitors. Thus, they constitute a class of materials of major industrial importance for many parties. The ether amine market has for that matter already been widely developed for several decades.

BACKGROUND OF THE INVENTION

Ether amines are conventionally synthesized by first reacting an alcohol with a nitrile compound, generally acrylonitrile, in the presence of a basic catalyst. A step of hydrogenation of the product obtained is then performed in order to isolate the targeted ether amine.

Thus, U.S. Pat. No. 5,196,589 describes a process for manufacturing an ether amine by first reacting an alcohol with acrylonitrile, in the presence of an alkaline catalyst. A step of hydrogenation is then performed in order to obtain the desired ether amine. The particular feature of this process lies in the fact that the alcohol, a compound comprising a number of carbon atoms ranging from 6 to 36, is in the presence of a stable free radical compound, thus making it possible especially to considerably reduce the production of undesired side products.

Patent EP 1219597, for its part, discloses a process for preparing an ether amine, comprising a first step of reacting a primary or secondary alcohol with acrylonitrile, in the presence of an alkali metal hydroxide, and then a second step of hydrogenation of the product obtained. The primary or secondary alcohol is a compound comprising a number of carbon atoms ranging from 6 to 24.

However, at a time when the environmental challenges are truly high, none of these documents indicates the use of any biosourced or biodegradable reagent having a good ecotoxicological profile.

In addition, it is known that particular ether amines, especially the commercial products Tomamine® PA-14 and Tomamine® DA-14, are used for the purpose of the selective removal of silicates during ore flotation.

It would thus be advantageous to provide an ether amine obtained from at least one biosourced and biodegradable reagent. It would also be advantageous for the use of such an ether amine to lead to a more selective removal of silicates during ore flotation than commercial ether amines.

SUMMARY OF THE INVENTION

The subject of the present invention is a compound of formula (I):

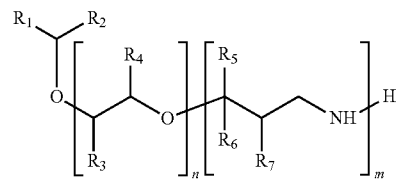

in which:
the groups $R_1$ and $R_2$, which may be identical or different, represent, independently of each other, a linear, branched or cyclic, saturated or unsaturated hydrocarbon-based group, comprising from 1 to 15 carbon atoms, preferably from 1 to 10 carbon atoms;
the groups $R_3$ and $R_4$, which may be identical or different, are chosen, independently of each other, from a hydrogen atom, a methyl group and an ethyl group;
the groups $R_5$, $R_6$ and $R_7$, which may be identical or different, are chosen, independently of each other, from a hydrogen atom and an alkyl group comprising from 1 to 6 carbon atoms, preferably from 1 to 4 carbon atoms, more preferably from 1 to 3 carbon atoms;
n is an integer ranging from 0 to 20;
m is an integer ranging from 1 to 6.

According to a preferred embodiment, when $R_1$ is a hexyl group, $R_2$ is a methyl group, n is equal to 0, $R_5$, $R_6$ and $R_7$ denote a hydrogen atom, then m is other than 1.

According to another preferred embodiment, the total number of carbon atoms in the groups $R_1$ and $R_2$ is between 5 and 20 carbon atoms, preferably between 6 and 20 carbon atoms.

A subject of the present invention is also a process for manufacturing the compound of formula (I) according to the invention.

Another subject of the invention is a compound of formula (V):

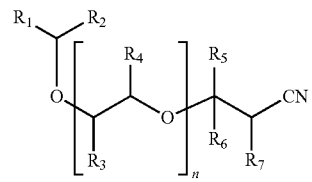

in which:
the groups $R_1$, $R_2$, $R_3$, $R_4$, $R_5$, $R_6$ and $R_7$ are as defined previously, and
n is as defined previously.

A subject of the present invention is also a compound of formula (VI):

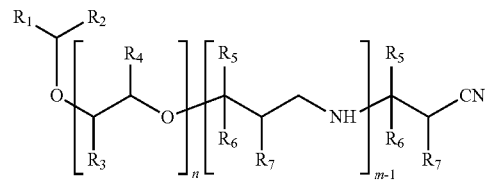

in which:

the groups $R_1$, $R_2$, $R_3$, $R_4$, $R_5$, $R_6$ and $R_7$ are as defined previously, and n and m are as defined previously.

Another subject of the present invention relates to the use of the compound according to the invention especially as an ore flotation collector.

DETAILED DESCRIPTION OF THE INVENTION

Other advantages and characteristics of the invention will emerge more clearly on examining the detailed description.

It is moreover pointed out that the expressions "between . . . and . . . " and "from . . . to . . . " used in the present description should be understood as including each of the mentioned limits.

The compound according to the invention is of formula (I) mentioned above.

Preferentially, n is an integer ranging from 0 to 10, more preferentially from 0 to 5, even more preferentially from 0 to 1.

Advantageously, the groups $R_3$ and $R_4$, which may be identical or different, are chosen, independently of each other, from a hydrogen atom and a methyl group.

Preferably, m is an integer ranging from 1 to 4; more preferentially, m is equal to 1, 2 or 3.

A subject of the invention is also a process for manufacturing the compound of formula (I) according to the invention, successively comprising:

a step of reacting a compound of formula (II):

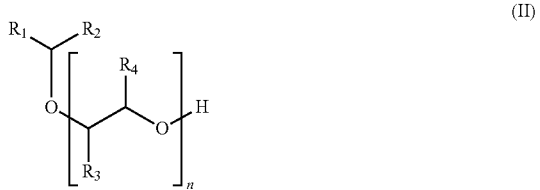

in which the groups $R_1$, $R_2$, $R_3$, $R_4$ and n are as defined previously;

with an α,β-unsaturated nitrile;

a hydrogenation reaction;

the product derived from these steps being able to react in series (m−1) times with the α,β-unsaturated nitrile, and then with dihydrogen, m being as defined previously.

According to a preferred embodiment, the α,β-unsaturated nitrile is chosen from acrylonitrile and methacrylonitrile, preferably acrylonitrile.

Thus, when n is equal to 0, the compound of formula (II) may be 2-octanol. This alcohol is of particular interest in several respects. Specifically, it is a biosourced, biodegradable product and has a good ecotoxicological profile. In addition, the boiling point of 2-octanol is high and its cost price is entirely reasonable.

Advantageously, the mole ratio of the α,β-unsaturated nitrile to the compound of formula (II) ranges from 0.8 to 1.2, preferably from 0.9 to 1.2.

Particularly advantageously, the mole ratio of the α,β-unsaturated nitrile to the compound of formula (II) ranges from 1.01 to 1.1, i.e. the reaction of the compound of formula (II) with the α,β-unsaturated nitrile is performed with a slight excess of α,β-unsaturated nitrile.

Preferentially, the reaction of the compound of formula (II) with the α,β-unsaturated nitrile is performed in the presence of at least one basic catalyst BC.

Preferably, the basic catalyst BC is chosen from alkali metal and alkaline-earth metal hydroxides, alkali metal alkoxides, alkali metal hydrides, basic resins and quaternary ammonium hydroxides.

Particularly preferably, the basic catalyst BC is chosen from sodium hydroxide, potassium hydroxide, sodium hydride and potassium hydride.

According to a particular embodiment of the invention, the amount of basic catalyst BC used ranges from 0.1% to 2% by weight, preferably from 0.5% to 1% by weight, relative to the total weight of the compound of formula (II).

The temperature for the reaction of the compound of formula (II) with the α,β-unsaturated nitrile may vary within wide proportions. Preferably, it ranges from 20 to 75° C., more preferentially from 25 to 70° C., even more preferentially from 25 to 65° C.

Advantageously, the reaction of the compound of formula (II) with the α,β-unsaturated nitrile is performed without a solvent, but it is also possible to use a solvent that is neutral with respect to the reaction of the compound of formula (II) with the α,β-unsaturated nitrile.

The term "solvent that is neutral with respect to the reaction" means any solvent that does not interact chemically with the reagents for the reaction of the compound of formula (II) with the α,β-unsaturated nitrile.

Preferably, the solvents that are neutral with respect to the reaction are chosen from ethers, dimethylformamide and aromatic solvents which dissolve the reagents, chosen from toluene and xylenes.

Where appropriate, the basic catalyst BC may be neutralized at the end of the reaction via any means known to those skilled in the art, for instance, and in a nonlimiting manner, an organic or mineral acid, preferably chosen from hydrochloric acid and acetic acid, or, alternatively, the catalyst may be removed, for example by filtration when it is of solid nature.

Preferably, the hydrogenation reaction is performed in the presence of at least one catalyst CT.

According to a particular embodiment, said catalyst CT is chosen from Raney nickel and Raney cobalt.

Advantageously, the amount of catalyst CT ranges from 0.5% to 10% by weight, preferably from 2% to 8% by weight, relative to the weight of the product derived from the reaction of the compound of formula (II) with the α,β-unsaturated nitrile.

Preferentially, the pressure during the hydrogenation reaction ranges from 1 to 10 MPa and preferably from 1.5 to 5 MPa.

Preferably, the temperature of the hydrogenation reaction ranges from 50 to 170° C. and preferably from 70 to 150° C.

According to a particular embodiment of the invention, in order to promote the formation of the primary amine, it may be envisaged to add an amount of ammonia that is capable of generating a partial pressure of ammonia. Advantageously, an ammonia/nitrile function mole ratio ranging from 0.5 to 2 is suitable for use. Alternatively, it is also possible to add a strong base, preferably chosen from sodium hydroxide and potassium hydroxide, in an amount that may range from 100 ppm to 5000 ppm, preferably from 500 to 5000 ppm, more preferentially from 500 to 2500 ppm, relative to the amount of product derived from the reaction of the compound of formula (II) with the α,β-unsaturated nitrile.

Particularly advantageously, the addition of said amount of ammonia that is capable of generating a partial pressure of ammonia and the addition of said strong base are combined.

Preferably, the successive steps of reaction of the compound of formula (II) with the α,β-unsaturated nitrile and the hydrogenation reaction are performed in the same reactor.

It is also possible to work in a solvent medium with organic or aqueous-organic solvents, for instance alcohols (methanol, ethanol or isopropanol) and any other solvent used for hydrogenation reactions and which dissolves the reagents and the final products.

It is possible to work in batch mode by introducing all of the reagents and conducting the hydrogenation reaction. It is also possible to work in semi-batch mode by introducing the solvent, the ammonia and/or the strong base, the catalyst and the hydrogen, and then by continuously introducing the condensation product derived from the reaction of the compound of formula (II) with the α,β-unsaturated nitrile.

Advantageously, the reaction of the compound of formula (II) with the β,β-unsaturated nitrile and the hydrogenation reaction are performed in different reactors.

Preferentially, the process according to the invention comprises, prior to the successive steps of reacting the compound of formula (II) with an α,β-unsaturated nitrile and of hydrogenation, a step of reacting an alcohol of formula (III):

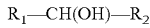

in which $R_1$ and $R_2$ are as defined previously, with n compound(s) of formula (IV):

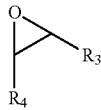

in which:
the groups $R_3$ and $R_4$ are as defined previously, and
n is as defined previously.

A subject of the invention is also the use of a compound of formula (I) as defined previously, as a lubricant, cationic surfactant, ore flotation collector, corrosion inhibitor, fuel additive and crosslinking agent for epoxy resins.

The use of the compound of formula (I) as an ore flotation collector is particularly preferred.

The invention is illustrated by the following examples, which are not in any way limiting.

EXAMPLES

The 2-octanol used is the refined-grade product sold by Arkema.

Example 1: Synthesis of 3-(2-octyloxy)propanamine

1) Synthesis of 3-(2-octyloxy)propionitrile a) Use of Potassium Hydroxide 130 g (1 M) of 2-octanol and 2 g of potassium hydroxide, as a 50% aqueous solution, are placed in a reactor equipped with a stirrer and fitted with a dropping funnel, a condenser, a system for inertizing with nitrogen and a heating jacket. The reaction medium is brought to 45° C. with stirring and under an inert atmosphere, and 55 g (1.04 M) of acrylonitrile are then added dropwise. The temperature is maintained after the addition until the reaction is complete. At the end of the reaction, the basic catalyst is neutralized by stoichiometry with hydrochloric acid. The propionitrile ether is isolated by thin-film distillation, in a molar yield of 90%.

b) Use of Sodium Hydride 130 g (1 M) of 2-octanol and 0.6 g of sodium hydride are placed in a reactor equipped with a stirrer and fitted with a dropping funnel, a condenser, a system for inertizing with nitrogen and a heating jacket. The reactor is purged with nitrogen to remove the hydrogen formed. The reaction medium is brought to 35° C. with stirring and under an inert atmosphere, and 55 g (1.04 M) of acrylonitrile are then added dropwise. The temperature is maintained after the addition until the reaction is complete. At the end of the reaction, the basic catalyst is neutralized by stoichiometry with hydrochloric acid. The propionitrile ether is isolated by thin-film distillation, in a molar yield of 91%.

2) Hydrogenation of 3-(2-octyloxy)propionitrile 183 g (1 M) of 3-(2-octyloxy)propionitrile obtained according to processes 1)a) or 1)b), 14 g of Raney nickel and 2000 ppm of KOH, as an aqueous 50% solution, are placed in a 300 cm³ Autoclave Engineer autoclave equipped with a stirring system of auto-suction turbomixer type, a cooling coil and a pressure and temperature regulation system. The autoclave is locked and purged with nitrogen. Hydrogen is then introduced during the temperature increase so that a total pressure of 3 MPa at 110° C. is obtained. The reaction is continued until there is no more consumption of hydrogen. At the end of the reaction, the catalyst is recovered by filtration. The crude reaction product is thin-film distilled to obtain 3-(2-octyloxy)propanamine in a molar yield of 85%.

Example 2: Synthesis of an Etherdiamine

1) Synthesis of 3-[3-(2-octyloxy)propylamine]propionitrile 225 g (1.2 M) of 3-(2-octyloxy)propanamine and 2.25 g of water are placed in a reactor equipped with a stirrer and fitted with a dropping funnel, a condenser, a system for inertizing with nitrogen and a heating jacket.

The reaction medium is brought to 60° C. With stirring and under an inert atmosphere, and 65 g (1.226 M) of acrylonitrile are then added dropwise. The temperature is maintained after the addition until the reaction is complete, i.e. about 2 hours. The 3-[3-(2-octyloxy)propylamine]propionitrile is obtained in a molar yield of 87%.

2) Hydrogenation of 3-[3-(2-octyloxy)propylamine]propionitrile 200 g (1 M) of 3-[3-(2-octyloxy)propylamine]propionitrile obtained according to the above process and 3.6 g of Raney nickel are placed in a 500 cm³ Autoclave Engineer autoclave equipped with a stirring system of auto-suction turbomixer type, a cooling coil and a pressure and temperature regulation system. The autoclave is locked and purged with nitrogen. The reaction medium is then heated to 75° C. Ammonia is introduced up to a total pressure of 0.8 MPa. Hydrogen is then introduced during the temperature increase so that a total pressure of 3 MPa at 120° C. is obtained. The reaction is continued until there is no more consumption of hydrogen. At the end of the reaction, the autoclave is degassed and the catalyst is recovered by filtration. The crude etherdiamine is obtained in a molar yield of 83%.

Example 3: Synthesis of a Polyether Amine

1) Synthesis of a tris(ether) propionitrile 262 g (1 M) of tris(ethoxyl) 2-octanol and 2 g of potassium hydroxide, as a 50% aqueous solution, are placed in a reactor equipped with a stirrer and fitted with a dropping funnel, a condenser, a system for inertizing with nitrogen and a heating jacket. The reaction medium is brought to 55° C. with stirring and under an inert atmosphere, and 55.6 g (1.05 M) of acrylonitrile are then added dropwise. The temperature is maintained after the addition until the reaction is complete. At the end of the reaction, the basic catalyst is neutralized by stoichiometry with hydrochloric acid. The tris(ether) propionitrile is obtained in a molar yield of 89%.

2) Hydrogenation of the tris(ether) propionitrile 252 g (0.8 M) of the tris(ether) propionitrile obtained according to the above process, 20 g of Raney nickel and 2000 ppm of potassium hydroxide, as an aqueous 50% solution, are placed in a 500 cm³ Autoclave Engineer autoclave equipped with a stirring system of auto-suction turbomixer type, a cooling coil and a pressure and temperature regulation system. The autoclave is locked and purged with nitrogen. Hydrogen is then introduced during the temperature increase so that a total pressure of 3 MPa at 120° C. is obtained. The reaction is continued until there is no more consumption of hydrogen. At the end of the reaction, the autoclave is degassed and the catalyst is recovered by filtration. The tris(ether)amine is obtained in a molar yield of 81%.

Example 4: Use of the Compound According to the Invention as a Flotation Collector A phosphate ore containing silicates is purified by reverse flotation. The tests are performed in an Outotec flotation cell.

In a first stage, 2.5 liters of tap water and 340 g of a ground phosphate ore (the particle size of which ranges from 30 to 300 μm) are introduced. The turbomixer speed is adjusted to 1500 rpm to ensure suspension of the ore in the entire volume of the cell. 0.34 g of phosphoric acid, as an aqueous 85% solution, is then added and stirring is continued for three minutes.

Next, 0.17 g of a carbonate collector provided by the company CECA under the trade name Melioran® P312 is added and stirring is continued for two minutes. Air is then fed into the cell at a flow rate of 3 L/minute and flotation is performed for two minutes. The foam is collected regularly with a spatula.

The air supply is switched off at the end of flotation and 10.2 g of cationic silicate collector are added. Stirring is continued for two minutes before switching the air supply back on. Flotation is performed for four minutes.

On conclusion of these two steps, the ore remaining in the flotation cell is filtered off on a Büchner funnel and dried in an oven overnight. The dried ore is then weighed to determine the amount recovered and sent for analysis to determine its composition.

The comparative tests relate to five cationic silicate collectors used in the second flotation step.

The starting ore is of fluoroapatite type containing 43% by weight of calcite and 17% by weight of quartz, relative to the total weight of the ore, as impurities. The content of $P_2O_5$ compound is 13.8% by weight relative to the weight of the ore.

Compound A is a comparative compound. It is Noramac® C26 (N-alkyl coconut amine acetate) sold by the company CECA.

Compound B is a comparative compound. It is Tomamine® PA-14 (isodecyloxypropylamine) sold by the company Air Products.

Compound C is a comparative compound. It is Tomamine® DA-14 (isodecyloxypropyl-1,3-diaminopropane) sold by the company Air Products.

Compound D is a compound according to the invention corresponding to formula (VII) below:

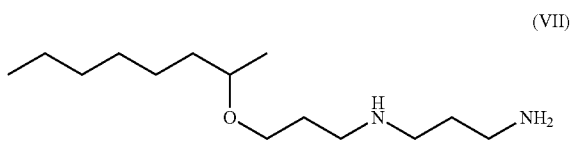 [SMILES: CCCCCCC(C)OCCCNCCCN]

(VII)

Compound E is a compound according to the invention corresponding to formula (VIII) below:

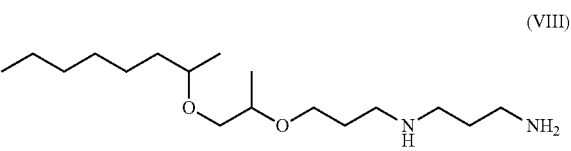 [SMILES: CCCCCCC(C)OCC(C)OCCCNCCCN]

(VIII)

The analysis results for the ore after flotation are collated in Table 1 below:

TABLE 1

| | Silicates removed (mass %) | Calcite removed (mass %) | Final content of $P_2O_5$ (mass %) |
| --- | --- | --- | --- |
| Compound A (comp.) | 12.1 | 65.2 | 20.5 |
| Compound B (comp.) | 29.4 | 76.4 | 22.8 |
| Compound C (comp.) | 78.5 | 64.9 | 25.6 |
| Compound D (inv.) | 81 | 86.6 | 29.6 |
| Compound E (inv.) | 81.6 | 82.9 | 28.6 |

Table 1 clearly shows that compounds D and E according to the invention make it possible to remove a larger amount of silicates than the three comparative compounds A, B and C.

In addition, the final content of $P_2O_5$ is greater by means of the use of compounds D and E than that associated with the use of the comparative compounds.

Thus, it has been demonstrated that the use of a compound according to the invention led to selective removal during the flotation of a phosphate ore. This property is even improved relative to the commercial products.

The invention claimed is:

1. A compound of formula (I):

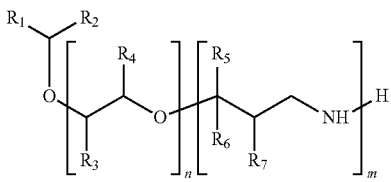

wherein:
the group $R_1$ is hexyl and the group $R_2$ is methyl;
the groups $R_3$ and $R_4$, which may be identical or different, are selected, independently of each other, from a hydrogen atom, a methyl group or an ethyl group;
the groups $R_5$, $R_6$ and $R_7$, which may be identical or different, are selected, independently of each other, from a hydrogen atom or an alkyl group comprising from 1 to 6 carbon atoms;
n is an integer ranging from 0 to 20, inclusive; and
m is an integer ranging from 1 to 6, inclusive.

2. The compound according to claim 1, wherein n is an integer ranging from 0 to 10, inclusive.

3. The compound according to claim 1 wherein the groups $R_3$ and $R_4$, which may be identical or different, are selected, independently of each other, from a hydrogen atom or a methyl group.

4. The compound according to claim 1 wherein m is an integer ranging from 1 to 4, inclusive.

5. A process for manufacturing a compound of formula (I) according to claim 1 comprising the steps of:
a) a step of reacting a compound of formula (II):

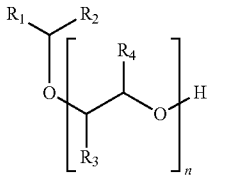

with an α,β-unsaturated nitrile;
b) a step of hydrogenation of the product of step a); and
c) when m is an integer greater than 1, reacting the product derived from step a) and step b) in series (m−1) times with the α,β-unsaturated nitrile, and then with dihydrogen, wherein $R_1$, $R_2$, $R_3$, $R_4$, m and n are as defined in claim 1.

6. The process according to claim 5, wherein the α,β-unsaturated nitrile is selected from acrylonitrile or methacrylonitrile.

7. The process according to claim 5 wherein the mole ratio of the α,β-unsaturated nitrile to the compound of formula (II) ranges from 0.8 to 1.2, inclusive.

8. The process according to claim 5 wherein the mole ratio of the α,β-unsaturated nitrile to the compound of formula (II) ranges from 1.01 to 1.1, inclusive.

9. The process according to claim 5 wherein the step a) reaction of said compound of formula (II) with the α,β-unsaturated nitrile is performed in the presence of at least one basic catalyst (BC).

10. The process according to claim 9, wherein the basic catalyst (BC) is selected from the group consisting of alkali metal hydroxides, alkaline-earth metal hydroxides, alkali metal alkoxides, alkali metal hydrides, basic resins, quaternary ammonium hydroxides, and mixtures thereof.

11. The process according to claim 5 wherein said process comprises, prior to the step a), a step of reacting an alcohol of formula (III):

wherein the group $R_1$ is hexyl and the group $R_2$ is methyl, with n compound(s) of formula (IV):

in which:
the groups $R_3$ and $R_4$, which may be identical or different, are selected, independently of each other, from a hydrogen atom, a methyl group or an ethyl group, and
n is an integer ranging from 0 to 20, inclusive, whereby the compound of Formula (II) is produced.

12. A method of manufacturing a lubricant, a cationic surfactant, an ore flotation collector, a corrosion inhibitor, a fuel additive, or a crosslinking agent for epoxy resins comprising incorporating the compound of formula (I) according to claim 1 into a lubricant, a cationic surfactant, an ore flotation collector, a corrosion inhibitor, a fuel additive, or a crosslinking agent for epoxy resins.

13. The compound according to claim 1, wherein n is equal to 0, $R_5$, $R_6$ and $R_1$ denote a hydrogen atom, and m is an integer ranging from 2 to 6.

* * * * *